United States Patent [19]

Frishberg

[11] 4,180,663

[45] Dec. 25, 1979

[54] METHINE DYE SYNTHESIS

[75] Inventor: Mark D. Frishberg, Kingsport, Tenn.

[73] Assignee: Eastman Kodak Company, Rochester, N.Y.

[21] Appl. No.: 19,677

[22] Filed: Mar. 12, 1979

Related U.S. Application Data

[63] Continuation of Ser. No. 820,959, Aug. 1, 1977, abandoned.

[51] Int. Cl.$^2$ .................. C07C 121/22; C07D 215/12; C07D 265/34
[52] U.S. Cl. .................................. 544/105; 8/162 R; 546/165; 260/326.5 R; 260/465 E; 548/165; 548/169; 548/210; 548/213
[58] Field of Search ........ 260/465 E, 304 A, 306.6 R, 260/326.5 R; 544/105; 546/165

[56] References Cited

U.S. PATENT DOCUMENTS

| | | | |
|---|---|---|---|
| 3,398,152 | 8/1968 | Wallace et al. | 546/165 |
| 3,917,604 | 11/1975 | Hoyle | 546/165 |

OTHER PUBLICATIONS

Fieser et al., Reagents for Organic Synthesis, vol. 1, frontispage, pp. 284–289 and 878, John Wiley & Sons, Inc. (1967).

*Primary Examiner*—John D. Randolph
*Attorney, Agent, or Firm*—Donald W. Spurrell; Daniel B. Reece, III

[57] ABSTRACT

A process for the preparation of a disperse methine dye containing at least one dicyanomethylidene group comprising the steps of (A) preparing an anhydrous solution of an aldehyde formed by contacting an aromatic amine, 1,2,3,4-tetrahydroquinoline or benzomorpholine compound capable of undergoing the Vilsmeier-Haack reaction with POCl$_3$ and a N,N-di-alkylformamide wherein the alkyl moiety is 1–4 carbon atoms;

(B) subsequently adding to said solution at least one equivalent of cyanoacetamide based on the equivalents of aldehyde formed in (A), thereby forming a reaction mixture of aldehyde and in situ generated malononitrile; and (C) adjusting the pH of the solution to a point sufficient for the condensation of the aldehyde and in situ generated malononitrile to occur thereby producing a disperse methine dye.

8 Claims, No Drawings

METHINE DYE SYNTHESIS

This invention relates to a novel process for making methine dyes containing a dicyanomethylidene group. This process involves the dehydration of cyanoacetamide to malononitrile with a dialkylamide and phosphorous oxychloride in the presence of an aldehyde (the term "aldehyde" as used throughout this specification and claims to describe the invention includes Vilsmeier adduct complex), prepared from an aromatic amine, 1,2,3,4-tetra-hydroquinoline or benzomorpholine compound capable of undergoing the Vilsmeier-Haack reaction, followed by a pH adjustment sufficient to allow the reaction of methine dye formation. The compounds thus prepared are useful as disperse dyes for dyeing synthetic fibers such as cellulose acetate and polyester fibers.

It is known that methine compounds, such as Color Index Disperse Yellows 88 and 89, can be prepared by treating an aromatic amine with an N,N-dialkylformamide and a dehydrating agent such as $POCl_3$, followed by drowning in water to obtain a formylated aromatic amine and then condensing the formyl compound with an active methylene compound in the presence of a basic catalyst. Such techniques are described extensively in the patent literature, e.g., U.S. Pat. No. 3,398,152. Since the reaction of the active methylene compound and the formyl compound generally requires essentially anhydrous conditions, the formyl compound must be isolated and dried or extracted with an organic solvent, both of which are time-consuming and therefore add considerably to the cost of the methine compound.

Furthermore, a general literature procedure for the synthesis of nitriles involves the dehydration of amides with phosphorous oxychloride and dimethylformamide. This procedure has not found utility for the preparation of malononitrile by the dehydration of cyanoacetamide since it has been claimed that malononitrile is unstable under these conditions and reacts with dimethylformamide to yield dimethylaminomethylenemalononitrile [Japanese Pat. No. 69 25570 (1969); C.A. 72:P12165g (1970)]. Dimethylaminomethylenemalononitrile does not react with aldehydes to yield methine dyes.

Additionally, it is known that methine dyes may be prepared by contacting a preformed anhydrous solution of an intermediate compound, formed by contacting an aromatic amine with $POCl_3$ and a di-lower-alkyl formamide, with an active methylene compound having the formula $NC-CH_2-R^2$. In the formula, the amine may be a monovalent or divalent residue of an aniline, 1,2,3,4-tetrahydroquinoline or benzomorpholine component of a disperse methine dye compound attached to the group $-CH=C(CN)R^2$ by an aromatic ring carbon atom in the position para to the aromatic amine nitrogen atom; $R^2$ is cyano or an acyl group derived from an organic, carboxylic or sulfonic acid. According to this process as claimed in U.S. Pat. No. 3,917,604, the utilization of that process avoids the necessity of isolating a formyl compound as is done in the known techniques mentioned above in the synthesis of methine compounds. This process will not result in the preparation of methine dyes containing a dicyanomethylidene group via the in situ generation of malononitrile as hereinafter described.

I have invented a novel process for the preparation of disperse methine dyes containing at least one dicyanomethylidene group comprising the steps of (A) preparing an anhydrous solution of an aldehyde formed by contacting an aromatic amine, 1,2,3,4-tetrahydroquinoline or benzomorpholine compound capable of undergoing the Vilsmeier-Haack reaction with $POCl_3$ and a N,N-dialkylformamide wherein the alkyl moiety is 1–4 carbon atoms;

(B) subsequently adding to said solution at least one equivalent of cyanoacetamide based on the equivalents of aldehyde formed in (A), thereby forming a reaction mixture of aldehyde and in situ generated malononitrile; and (C) adjusting the pH of the solution to a point sufficient for the condensation of the aldehyde and in situ generated malononitrile to occur thereby producing a disperse methine dye.

The compounds which may be prepared by the process of this invention are well known in the art of disperse methine dyes. The following are some of the patents disclosing methine dyes.

| | | |
|---|---|---|
| U.S. 1,950,421 | U.S. 2,850,520 | U.S. 3,435,062 |
| U.S. 2,053,819 | U.S. 2,914,551 | U.S. 3,453,280 |
| U.S. 2,166,487 | U.S. 3,027,220 | U.S. 3,504,010 |
| U.S. 2,179,895 | U.S. 3,189,641 | U.S. 3,555,016 |
| U.S. 2,206,108 | U.S. 3,240,783 | British 1,036,079 |
| U.S. 2,583,551 | U.S. 3,247,211 | British 1,049,315 |
| U.S. 2,649,471 | U.S. 3,326,960 | British 1,053,997 |
| U.S. 2,766,233 | U.S. 3,349,098 | British 1,138,582 |
| U.S. 2,776,310 | U.S. 3,386,491 | British 1,138,583 |
| U.S. 2,789,125 | U.S. 3,390,168 | British 1,173,679 |
| U.S. 2,811,544 | U.S. 3,422,133 | Belgian 703,661 |

Of these dyes, those containing at least one dicyanomethylidene group may be prepared in accordance with this process.

In general, the above compounds which can be prepared by the process of the invention conform to the following structures:

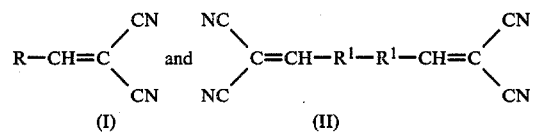

wherein the compounds of Formulas (I) and (II) and residues R and $-R^1-R^1-$ are well known in the art of disperse methine dyes.

The most common of the aromatic residues represented by R and $R^1$ are aniline, 1,2,3,4-tetrahydroquinoline, and, to a lesser extent, benzomorpholine residues. Typical of such aniline and tetrahydroquinoline residues are the groups having the formulas

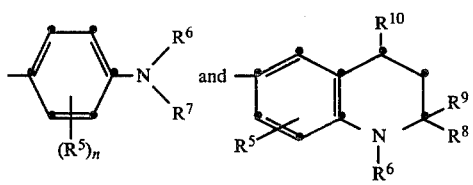

in which $R^5$ is hydrogen, lower alkyl, lower alkoxy or halogen; n is 0, 1 or 2; $R^6$ and $R^7$ are unsubstituted or substituted alkyl containing up to about 12 carbon atoms; cyclohexyl; unsubstituted or substituted aryl; or when $R^7$ is phenyl $R^6$ can be hydrogen; and $R^8$, $R^9$ and $R^{10}$ are hydrogen or lower alkyl. As used herein to describe an alkyl group or a group containing an alkyl moiety, "lower" designates a carbon content of up to about 4 carbon atoms. The aryl groups referred to herein include phenyl and phenyl substituted with non-ionic substituents such as lower alkyl, lower alkoxy, halogen, lower alkoxycarbonyl, cyano, carbamoyl, etc.

The $R^1$ moieties of the —$R^1$—$R^1$— residues of methine compounds (II) i.e., bismethine compounds can be joined by a common nitrogen atom as disclosed in U.S. 3,189,641 or by various aliphatic groups which can contain within them aryl and cycloalkyl groups as disclosed in U.S. Pat. Nos. 3,386,591, 3,504,010, 3,597,434, and Belgian No. 703,661. Representative of the residues represented by —$R^1$—$R^1$— are groups conforming to the formulas

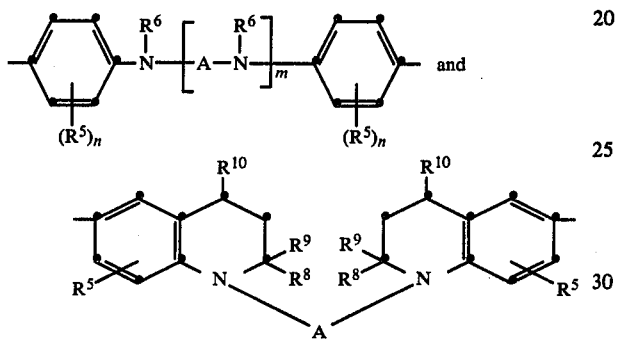

wherein each $R^5$, $R^6$, $R^8$, $R^9$ and $R^{10}$ can be the same or different groups as defined above, m is 0 or 1 and A is a divalent group having the formula —$R^{11}$—B—$R^{12}$— in which $R^{11}$ and $R^{12}$ are lower alkylene groups and B is a divalent radical such as oxygen, sulfur, sulfonyl, a dicarboxylic acid ester residue, a diisocyanate residue, a dicarboxylic acid amide residue, etc. The group —$R^1$—$R^1$— also can be joined benzomorpholine groups or the $R^1$ groups can be different, e.g., an aniline residue joined to a tetrahydroquinoline residue.

Preferred groups represented by —R and —$R^1$—$R^1$— are those encompassed by the general formulas

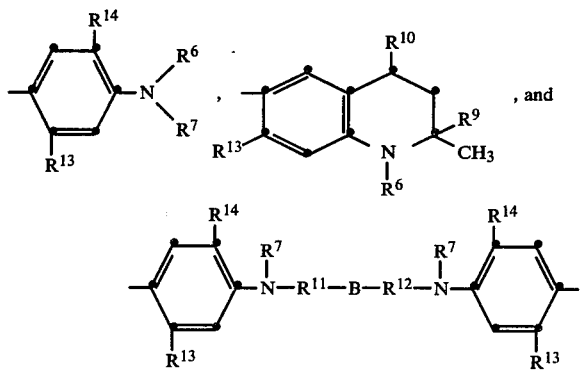

wherein
$R^{13}$ is hydrogen, methyl, methoxy, ethoxy or chlorine;
$R^{14}$ is hydrogen, methyl, methoxy or ethoxy;
$R^6$ is lower alkyl; phenethyl; cyclohexylmethyl; benzyl; benzyl substituted with lower alkyl, lower alkoxy, chlorine, bromine or lower alkoxycarbonyl; aryl; or a group having the formula —$R^{11}$—$R^{15}$ in which $R^{11}$ is ethylene, propylene, trimethylene or tetramethylene and $R^{15}$ is lower alkanoyloxy, cyano, lower alkoxycarbonyloxy, arylcarbamoyloxy, lower alkylcarbamoyloxy, aroyloxy, lower alkoxycarbonylbenzoyloxy, lower alkoxy, chlorine, aryloxy, 2-benzothiazolylthio, or a group having the formula

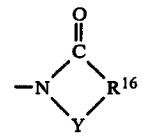

in which Y is —CO—, —SO$_2$—, and $R^{16}$ is ethylene, propylene, trimethylene or o-arylene;

$R^7$ is lower alkyl; cyclohexyl; lower alkylcyclohexyl; benzyl; benzyl substituted with lower alkyl, lower alkoxy, chlorine or bromine; aryl, or a group having the formula —$R^{11}$—$R^{17}$ in which $R^{11}$ is ethylene, propylene, trimethylene or tetramethylene and $R^{17}$ is lower alkanoyloxy, lower alkoxycarbonyloxy, aroyloxy or lower alkoxy;

$R^9$ and $R^{10}$ each is hydrogen or methyl;

$R^{11}$ and $R^{12}$ each is ethylene, propylene, trimethylene or tetramethylene; and B is a divalent group having the formula —Z—$R^{18}$—Z— in which Z is

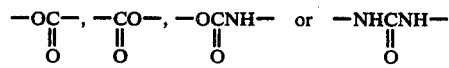

and $R^{18}$ is alkylene or one to six carbon atoms, phenylene or phenylene substituted with methyl;

in which each aryl moiety is phenyl, tolyl, lower alkoxyphenyl, or chlorophenyl.

The advantages of the present invention over the prior art processes are many. Cyanoacetamide is commercially a more advantageously economic starting material than malononitrile, the compound usually utilized in the preparation of commercial dyes. The storage and handling advantages of cyanoacetamide are great in that malononitrile is a waxy solid, melting at 32° C., and must be melted before use. Further, it is thermally unstable above 130° C., whereas cyanoacetamide is thermally stable and a good solid, melting point 118° to 120° C. Furthermore, the toxicity of cyanoacetamide is much lower than that of malononitrile, LD$_{50}$ (oral, rat) 1680 mg/Kg. vs. 61 mg/Kg., respectively. Additionally, the in situ preparation and use of malononitrile in the process of this invention represents a considerable increase in the usable yield of malononitrile with respect to other processes based on the dehydration of cyanoacetamide (Fieser, L.F. and Fieser, M., Reagents for Organic Synthesis, John Wiley and Sons, Inc., New York, 1967, page 878).

The process of the present invention is outlined below where "A" represents any N,N-dialkylaniline or tetrahydroquinoline or other benzene or heterocyclic aromatic nucleus that is suitably substituted to undergo a Vilsmeier-Haack formylation reaction.

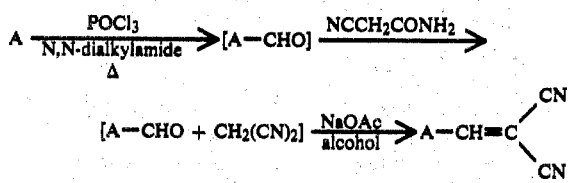

The additional phosphorous oxychloride and N,N-dialkylamide required for the dehydration step may be added at the Vilsmeier formylation step, preferably, or else with the cyanoacetamide. Those compounds capable of undergoing the Vilsmeier-Haack formylation reaction are well known in the art. See Maheas, M-R, Bull. Soc. Chim France, 1962, pp 1989–1999.

For the process of the invention to be economically feasible, at least one mole of cyanoacetamide is used per mole of intermediate formed in step A, and 0.5 mole of intermediate compound derived from the H—R$^1$—R$^1$—H amine previously mentioned. Advantageously, this step will require the use of a 10–20% excess of cyanoacetamide, although a greater amount can be used. The dehydration step B can be run at a temperature within the range of about −10° C. to about 50° C. for 2 to 24 hours, preferably at 25°–30° C. for 4 hours. At temperatures above about 30° C.–40° C. and for periods greater than 4 to 6 hours, the process as described in C.A. 72:P121655 (1970) becomes competitive, resulting in decreased yields of methine dye. It is emphasized the temperature range over which the process of the invention may be carried out is important, depending on the intermediates involved. Although it is not advantageous, the process can be carried out at pressures moderately above or below atmospheric pressure. Furthermore, the phosphorous oxychloride used in the dehydration step may be used in the amount of 0.5–1.5 mole percent of the cyanoacetamide used, preferably 0.7–0.8 mole percent.

The N,N-dialkylamide usage may be increased from 0 to 200 percent over that used in the formylation step, typically 50 to 100 percent.

The methine dye forming step is best carried out in the presence of an acid acceptor. Examples of such acid acceptors include alkali metal salts of lower carboxylic acids such as sodium and potassium acetate, alkali metal carbonates and bicarbonates such as sodium carbonate, potassium carbonate, sodium bicarbonate and potassium bicarbonate, alkali metal hydroxides such as sodium and potassium hydroxide and tertiary amines such as tri-lower alkylamines and pyridine. The amount of acid acceptor which will give the best results will vary depending on the acid acceptor used, the amount of POCl$_3$ used in synthesizing the intermediate compound and the particular aromatic amine used in preparing the intermediate compound. Although the optimum amount of acid acceptor can be readily determined experimentally, the use of at least about three to four mole equivalents of acid acceptor per mole of POCl$_3$ used in the synthesis of the intermediate compound gives superior results. For example, the use of one mole of POCl$_3$ in the synthesis of the intermediate compound will generally require, for best yields, at least 3 to 4 moles of sodium acetate or sodium bicarbonate and at least 1.5 to 2 moles of sodium carbonate. The use of more than the optimum amount of acid acceptor is not detrimental although it can add to the cost of the methine compound product.

A preferred embodiment of the invention comprises the addition of the DMF solution of the intermediate aldehyde and in situ prepared malononitrile to a solution or slurry of the acid acceptor in a water-miscible organic solvent. The performance of the physical steps of the process in this manner simplifies the isolation of the methine product essentially free of impurities. To isolate the product, water is added to effect complete precipitation of the product followed by filtration. Examples of the water-miscible solvents which can be used include the lower alkanols such as methanol, ethanol, propanol, and isopropanol, glycols such as ethylene glycol, propylene glycol and diethylene glycol, glycol ethers such as 2-methoxyethanol, 2-ethoxyethanol, and diethylene glycol dimethyl ether, di-lower-alkylalkanoylamides such as DMF and dimethylacetamide, and tri-lower alkylphosphate such as triethylphosphate. Phosphates and possibly other by-products formed during the process occasionally precipitate as a gelatinous material in cold or room temperature water. This by-product precipitate is soluble in hot (at least 50° C.) water and thus can be removed from the product by washing it with hot water.

The process of the invention is further illustrated by the following examples.

EXAMPLE 1

N-(β-Hydroxyethyl)-2,2,4-trimethyl-1,2,3,4-tetrahydroquinoline (10.9 g., 0.05 m.) was dissolved in 50 ml. of dimethylformamide. Phenyl isocyanate (6.54 g., 0.055 m.) was added and the mixture was heated on a steam bath for two hours. After cooling to 20° C., phosphorous oxychloride (14.3 g., 0.094 m.) was added dropwise at 20°–30° C. and the reaction mixture was heated at 45°–55° C. for 1½ hour. The mixture was cooled to 20° C. and cyanoacetamide (4.62 g., 0.055 m.) was added portionwise. After stirring at 20°–30° C. (some external cooling necessary) for four hours, the mixture was added dropwise to sodium acetate (40 g., 0.49 m.) in isopropanol (100 ml.) at 25°–40° C. When addition was complete, the temperature was held at 55°–60° C. for one hour. External heating was removed and water (80 ml.) was added dropwise with stirring. The mixture was cooled to 20° C. and the solid was collected by filtration, washed with isopropanol, cold water, and hot water and air-dried. The yield of dye was 17.2 g. (0.042 m., 83%) as a yellow-orange microcrystalline solid and has the following structure

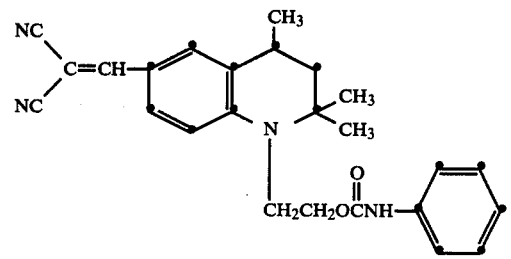

EXAMPLE 2

N-(β-Hydroxyethyl)-2,2,4-trimethyl-1,2,3,4-tetrahydroquinoline (10.9 g., 0.050 m.) was dissolved in 40 ml. of dimethylformamide. Phenyl isocyanate (6.54 g., 0.055 m.) was added and the mixture was heated on a steam bath for two hours. After cooling to 20° C., phosphorus oxychloride (8.4 g., 0.055 m.) was added dropwise at 20°–30° C. and the reaction mixture was heated at 40°–50° C. for 1¼ hour. The mixture was cooled to 20° C. and cyanoacetamide (4.6 g., 0.055 m.) and dimethylformamide (10 ml.) was added followed by the dropwise addition of phosphorus oxychloride (5.9 g., 0.038 m.) at 20°–30° C. The reaction mixture was stirred at 20°–30° C. The reaction mixture was stirred at 20°–30° C. (some external cooling necessary) for four hours and was added dropwise to a mixture of sodium acetate (40 g., 0.49 m.) in isopropanol (100 ml.) at 30°–45° C. After addition was complete, the temperature was held at 50°–60° C. for one hour. External heating was removed and water (80 ml.) was added dropwise with stirring. The mixture was cooled to 20° C. and the solid was collected by filtration, washed with isopropanol, cold water, and hot water and air-dried. The yield of dye was 17.4 g. (0.042 m., 84.5%) as a yellow-orange microcrystalline powder.

The invention has been described in detail with particular reference to certain preferred embodiment thereof, but it will be understood that variations and modifications can be effected within the spirit and scope of the invention.

I claim:

1. Process for the preparation of a disperse methine dye containing at least one dicyanomethylidene group comprising the steps of
   (A) preparing an anhydrous solution of an aldehyde formed by contacting an aromatic amine, 1,2,3,4-tetrahydroquinoline or benzomorpholine compound capable of undergoing the Vilsmeier-Haack reaction with $POCl_3$ and a dialkylformamide wherein the alkyl moiety is 1–4 carbon atoms;
   (B) subsequently adding to said solution at about 15° C. to about 40° C., at least one equivalent of cyanoacetamide based on the equivalents of aldehyde formed in (A), thereby forming a reaction mixture of aldehyde and in situ generated malonitrile; and
   (C) adjusting the pH of the solution to a point sufficient for the condensation of the aldehyde and in situ generated malononitrile to occur thereby producing a disperse methine dye.

2. Process of claim 1 wherein the aldehyde is formed from an aromatic amine.

3. Process of claim 1 wherein the aldehyde is formed from a 1,2,3,4-tetrahydroquinoline compound.

4. Process of claim 1 wherein the aldehyde is formed from a benzomorpholine compound.

5. Process of claim 1 wherein the dialkylformamide is dimethylformamide.

6. Process of claim 2 wherein the dialkylformamide is dimethylformamide.

7. Process of claim 3 wherein the dialkylformamide is dimethylformamide.

8. Process of claim 4 wherein the dialkylformamide is dimethylformamide.

* * * * *